United States Patent
Choi et al.

(10) Patent No.: US 6,265,443 B1
(45) Date of Patent: *Jul. 24, 2001

(54) METHOD FOR TREATING NEURONAL INJURY WITH CARBOXYFULLERENE

(75) Inventors: Dennis Wonkyu Choi, St. Louis; Laura Dugan; Tien-Sung Tom Lin, both of Chesterfield, all of MO (US); Tien-Yau Luh, Taipei (TW)

(73) Assignee: Washington University, St. Louis, MO (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/867,378

(22) Filed: Jun. 2, 1997

Related U.S. Application Data

(60) Provisional application No. 60/018,899, filed on Jun. 3, 1996, and provisional application No. 60/037,007, filed on Jan. 31, 1997.

(51) Int. Cl.$^7$ .......................... A61K 31/19; C07C 309/00
(52) U.S. Cl. ............................................ 514/569; 562/100
(58) Field of Search ............................................... 514/569

(56) References Cited

U.S. PATENT DOCUMENTS 5,648,523 * 7/1997 Chiang ................................. 562/100

FOREIGN PATENT DOCUMENTS

96/36631   11/1996  (WO).

OTHER PUBLICATIONS

Hersch et al., "Fullerene Chemistry in three Dimensions: Isolation of Seven Regioisometric Bisadducts and Chiral Trisadducts of C60 and DI(Ethoxycarbonyl) Methylene", Angewandte Chemie Int. Ed. Engl., vol. 33, No. 4 pp. 437–438 (1994).
M. Beal, "Does Impairment of Energy Metabolism Result in Excitotoxic Neuronal Death in Neurodegenerative Illnesses?", Ann. Neurol. 31: 119–130 (1992).
Braughler et al., "Central Nervous System Trauma and Stroke", Free. Radic. Biol. Med. 6:289–301 (1989).
Chan et al., "Cellular and molecular effects of polyunsaturated fatty acids in brain ischemia and injury", Prog. Brain Res. 63:227–235 (1985).
Chan et al., "Attenuation of Glutamate–induced Neuronal Swelling and Toxicity in Transgenic Mice Overexpressing Human CuZn–Superoxide Dismutase", Acta Neurochirurgica. 51:245–247 (1990).
Chan et al., "Cold–induced Brain Edema and Infarction are Reduced in Transgenic Mice Overexpressing CuZn–Superoxide Dismutase", Ann. Neurol. 29:482–486 (1991).
Choi et al., "Glutamate Neurotoxicity and Diseases of the Nervous System", Neuron 1:623–634 (1988).
Chow et al., "Trolox attenuates cortical neuronal injury induced by iron, ultraviolet light, glucose deprivation, or AMPA", Brain Res. 639:102–108 (1994).
Coyle et al., "Oxidative Stress, Glutamate, and Neurodegenerative Disorders", Science 262:689–694 (1993).
Dessi et al., "Regional variability in DNA fragmentation after global ischemia evidenced by combined histological and gel electrophoresis observations in the rat brain", J. Neurochem. 61:1973–1976 (1993).
Dugan et al., "NMA Receptor–induced membrane Fluidity Changes may Modulate Calcium influx in Cortical Neurons", Soc. Neurosci. Abs. 18:756, No. 321.5 (1992).
Dykens et al., "Mechanism of Kainate Toxicity to Cerebellar Neurons In vitro is Analagous to Reperfusion Tissue Injury", J. Neurochem. 49:1222–1228 (1987).*
Faden et al., "A potential role for excitotoxins in the pathophysiology of spinal cord injury", Ann. Nuerol. 23:623–626 (1988).*
Flamm et al., "Free Radicals in Cerebral Ischemia", Stroke 9:445–447 (1978).*
Franklin et al., Inhibition of Programmed Neuronal Death by Spin Traps: Evidence of a Role for Reactive Oxygen in Neuronal Apoptosis, Soc. Neurosci. Abs. 20:432 No. 188.7 (1994).*
Goldberg et al., "Combined oxygen and glucose deprivation in cortical culture: calcium–dependent and calcium–independent mechanisms of neuronal injury", J. Neurosci. 13:3510–3524 (1993).*
Greenamyre et al., "Alterations in L–Glutamate Binding in Alzeimer's and Huntington's Diseases", Science 227:1496–1498 (1985).*
Griffiths et al., "Status Epilepticus: The Reversibility of Calcium Loading and Acute Neuronal Pathological Changes in the Rat Hippocampus", Neurosci. 12:557–567 (1984).*
B. Halliwell, "Reactive Oxygen Species and the Central Nervous System", J. Neurochem. 59:1609–1623 (1992).*
Hirsch et al., "Fullerene Chemisty in Three Dimensions: Isolation of Seven Regioisomeric Bisadducts and Chiral Trisadducts of $C_{60}$ and Di)ethoxycarbonyl)methylene", Angew. Chem . Int. Ed. Engl. 33:437–438 (1994).*
Hockenbery et al., Bci–2 Functions in an Antioxidant Pathway to Prevent Apoptosis Cell 75:241–251 (1993).*
Imaizumi et al., Liposome–Entrapped Superoxide dismutase Reduces Cerebral Infarction in Cerebral Ischemia in Rats, Stroke 21:1312–1317 (1990).*

(List continued on next page.)

Primary Examiner—Theodore J. Criares
(74) Attorney, Agent, or Firm—George W. Johnston; Dennis P. Tramaloni; Joseph P. Kirk, Jr.

(57) ABSTRACT

A method of treating neurotoxic injury, where the injury is the result of the release of oxygen-derived free radicals, is disclosed. The method utilizes carboxyfullerenes as free radicals scavengers to reduce the damage caused by the free radicals.

28 Claims, 12 Drawing Sheets-

OTHER PUBLICATIONS

Figure 1A:
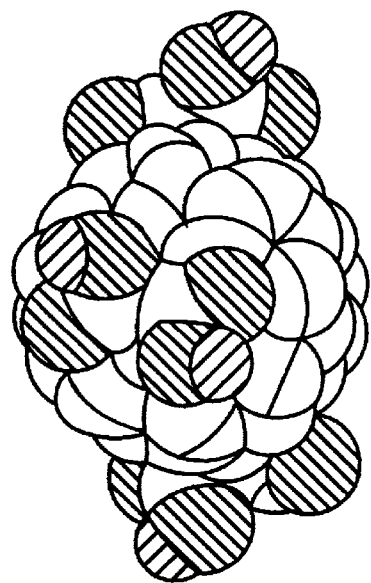

Kinouchi et al., "Attenuation of focal cerebral ischemic injury in transgenic mice overexpressing CuZn superoxide dismutase", Proc. Natl. Acad. Sci. USA 88:11158–11162 (1991).*

Kontos et al., "Superoxide production in experimental brain injury", J. Neurosurg. 64:803–807 (1986).*

Lafon–Cazal et al., "NMDA–dependent superoxide production and neurotoxicity", Nature 364:535–537 (1993).*

Lesiuk et al., "Effect of U74006F on Forebrain Ischemia in Rats", Stroke 22:896–901 (1991).*

Liu et al., "Polyethylene glycol–conjugated superoxide dismutase and catalase reduce ischemic brain injury", Amer. J. Physiol. 256:H589–593 (1989).*

MacManus et al., "DNA damage consistent with apoptosis in transient focal ischaemic neocortex", Neuroreport 5:493–496 (1994).*

B. Meldrum, "Possible therapeutic applications of antagonists of excitatory amino acid neurotransmitters", Sci. 68:113–122 (1985).*

Meldrum et al., "Excitatory amino acid neurotoxicity and neurodegenerative disease", Trends Pharmacol. Sci. 11:379–387 (1990).*

Mochizuki et al., "Apoptosis is induced by 1–methyl–4–phenylpyridinium ion (MPP+) in ventral mesencephalic–striatal co–culture in rat", Neurosci. Lett. 170:191–194 (1994).*

Monyer et al., "21–Aminosteroids Attenuate Excitotoxic Neuronal Injury in Cortical Cell Cultures", Neuron 5:121–126 (1990).*

C. W. Olanow, "Oxidation reactions in Parkinson's disease", Neurology 40:32–37.*

Ratan et al., "Oxidative Stress Includes Apoptosis in Embryonic Cortical Neurons", J. Neurochem. 62:376–379 (1994).*

M. Raff, "Social controls on cell Survival and Cell Death", Nature 356:397–400 (1992).

Rosenthal et al., "Prevention of Post–Ischemic Brain Lipid Conjugated Diene Production and Neurological Injury by Hydroxyethyl Starch–conjugated Deferoxamine", Free Rad. Biol. Med. 12:29–33 (1992).

Rothman et al., "Glutamate and the Pathophysiology of Hypoxic–Ischemic Brain Damage", Ann. Neurol. 19:105–111 (1986).

Sheardown et al., "2,3–Dihydroxy–6–nitro–7–Sulfamoyl–benzo(F)quinoxaline: A Neuroprotectant for Cerebral Ischemia", Science 247:571–574 (1990).

Siesjo et al., "Free Radicals and Brain Damage", Cerebrovasc. Brain Metab. Rev. 1:165–211 (1989).

Siesjo et al., Neuronal cell damage in the brain: possible involvement of oxidative mechanisms, Acta Physiol. Scand. [Suppl] 492:121–128 (1980).

Simon et al., "Blockade of N–Methyl–d–Aspartate Receptors May Protect Against Ischemic Damage in the Brain", Science 226:850–852 (1984).

Bernard W. Stewart, J. "Mechanisms of Apoptosis: Integration of Genetic, Biochemical, and Cellular Indicators", Natl. Cancer Inst. 86:1286–1295 (1994).

M. Anthony Verity, "Oxidative Damage and Repair in the Developing Nervous System", Neurotoxicol. 15:81–91 (1994).

Yue et al., "Neuroprotective effects of phenyl–t–butyl–nitrone in gerbil global brain ischemia and in cultured rat cerebellar neurons", Brain Res. 574:193–197 (1992).

* cited by examiner

O-3a (C₃ SYMMETRY)

R-3B (D₃ SYMMETRY)

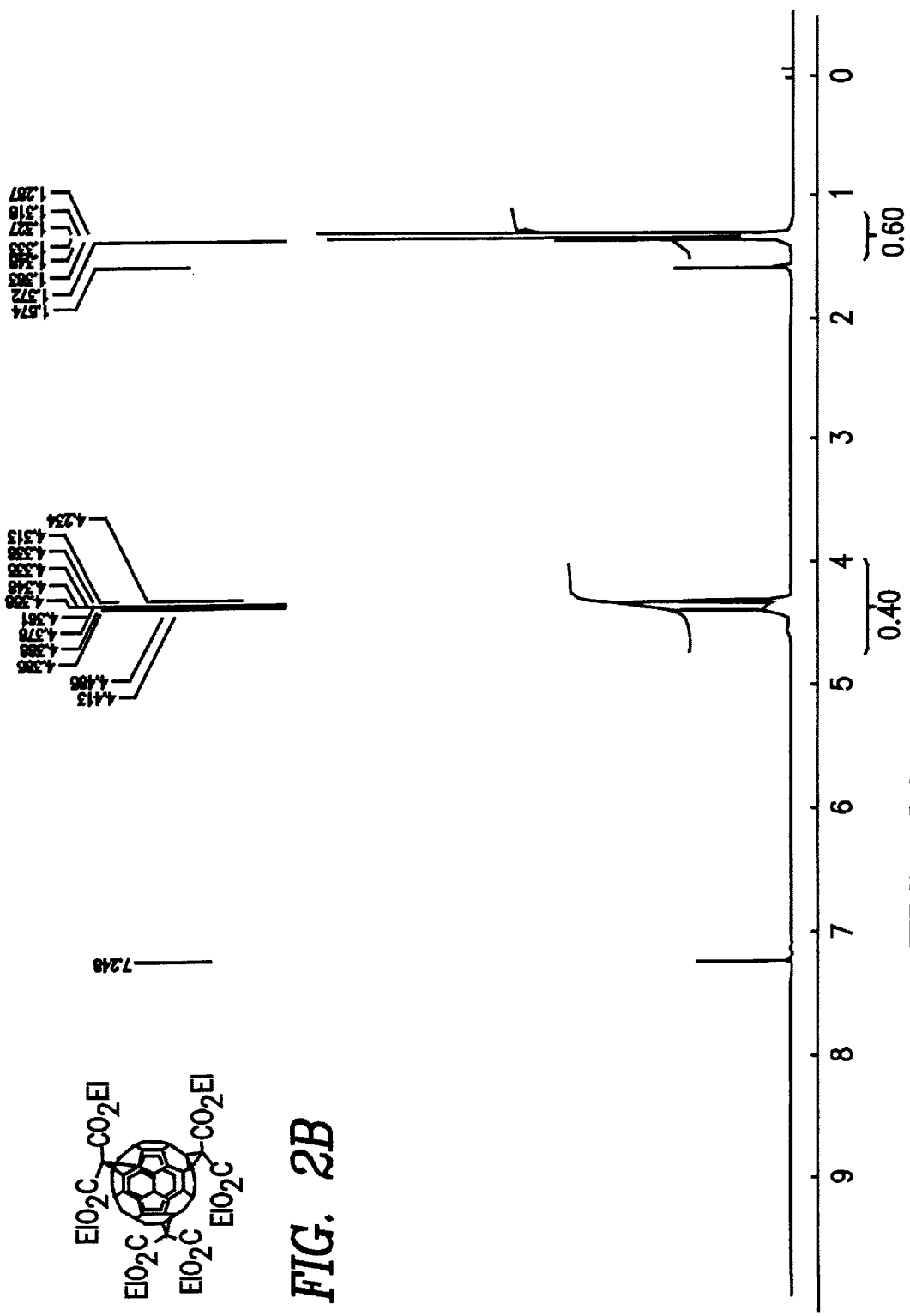

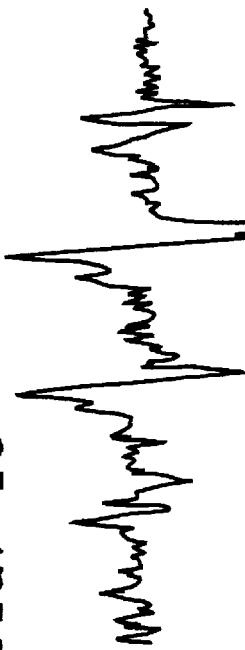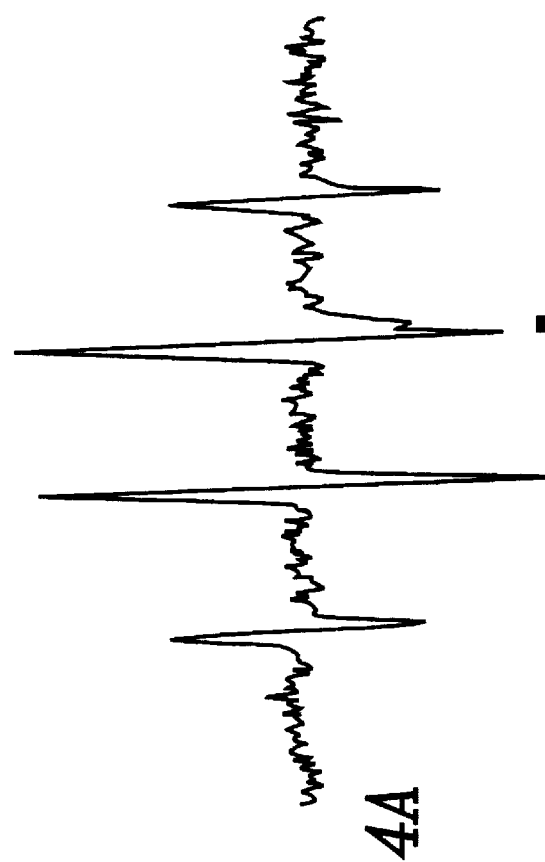
EPR SPECTRA
FIG. 4A  FIG. 4B  FIG. 4C  FIG. 4D  FIG. 4E

METHOD FOR TREATING NEURONAL INJURY WITH CARBOXYFULLERENE

This application claims benefit of U.S. Provisional application Ser. Nos. 60/018,899, filed Jun. 3, 1996, and 60/037,007, filed Jan. 31, 1997.

This invention was made partially with government support under grant number NIA 645K awarded by the National Institutes of Health. The government has certain rights to this invention.

BACKGROUND OF THE INVENTION

Glutamate, the main excitatory neurotransmitter in the central nervous system, is necessary for many normal neurological functions, including learning and memory. Overactivation of glutamate receptors, however, and resulting excitotoxic neuronal injury, has been implicated in the pathogenesis of neuronal loss in the central nervous system (CNS) following several acute insults, including hypoxia/ischemia (Simon et al., 1984; Meldrum, 1985; Rothman and Olney, 1986; Sheardown et al., 1990), trauma (Faden and Simon, 1988), epilepsy (Griffiths et al., 1984), and certain neurodegenerative disorders (Greenamayre et al., 1985; Choi, 1988; Meldrum and Garthwaite, 1990; Olanow, 1990; Beal, 1992).

Oxidative stress, caused by reactive oxygen species, represents another injury mechanism implicated in many of the same acute and chronic diseases (Flamm et al., 1978; Chan et al, 1985; Kontos and Wei, 1986; Siesjo et al., 1989; Braughler and Hall, 1989; review Halliwell, 1992). Reactive oxygen species (e.g., superoxide radical) would cause oxidative damage to cellular components, such as peroxidation of cell membrane lipids, inactivation of transport proteins, and inhibition of energy production by mitochondria (Halliwell, 1992).

These two events, glutamate excitotoxicity and oxidative stress, may be interlinked; reactive oxygen species formation may occur as a direct consequence of glutamate receptor overstimulation (Dugan et al., 1992; Lafon-Cazal et al., 1993) and thus mediate a component of glutamate neurotoxicity (Choi, 1988; Coyle and Puttfarcken, 1993). Excitotoxicity, in turn, can be reduced by free radical scavengers, including C, Zn-superoxide dismutase and catalase (Dykens et al., 1987; Chan et al., 1990), the 21-aminosteroid "lazaroids" (Monyer et al., 1990), the vitamin E analog, trolox (Chow et al, 1994), spin-trapping agents such as phenylbutyl-N-nitrone (Yue et al., 1992), and the ubiquinone analog, idebenone (Bruno et al., 1994) which reduce the amount of reactive oxygen species.

Free radical scavengers are neuroprotective in in vitro as well as in vivo models of traumatic or hypoxic/ischemic CNS injury. N-methyl-D-aspartate and AMPA/kainate receptor antagonists are neuroprotective in oxygen-glucose deprivation injury in vitro (Choi, 1988; Goldberg and Choi, 1993), and reduce loss of brain tissue in animal models of ischemia (Simon et al., 1984; Sheardown et al., 1990). Free radical scavengers also protect against excitotoxic neuronal death in vitro (Dykens et al., 1987; Monyer et al., 1990), and reduce ischemic injury in vivo (Liu et al., 1989; Imaizumi et al., 1990; Lesiuk et al., 1991; Rosenthal et al., 1992). Transgenic animals which overexpress the free radical scavenger enzyme, CuZn superoxide dismutase (SOD), are resistant to glutamate toxicity (Chan et al., 1990), and ischemic brain injury (Chan et al., 1991; Kinouchi et al., 1991).

Programmed cell death, or apoptosis, also contributes to cell death in certain neurologic disease states. For example, apoptosis would mediate delayed neuronal degeneration days after ischemia-reperfusion (Dessi et al., 1994; McManus et al., 1994), and would be a factor in neuronal cell death in certain neurodegenerative diseases (Mochizuki et al., 1994). Oxidative stress due to free radical oxygen species would be one of the insults that can trigger apoptosis (Raff, 1992; Verity, 1994; Stewart, 1994), so that free radical scavengers would also be able to limit programmed cell death (Ratan et al., 1994; Franklin et al., 1994). Bcl-2 appears to act on a free radical scavenging pathway to mediate its cytoprotective effects against apoptosis (Hockenbery et al., 1993).

SUMMARY OF THE INVENTION

We have discovered that carboxylated derivatives of $C_{60}(C(COOH)_2)_n$, wherein $C_{60}$ is buckminsterfullerene and n is an integer from 1 to 4 are biological free radical scavengers and neuroprotective agents, and so inhibit glutamate receptor-mediated neuronal injury and serum-deprivation-induced apoptotic neuronal death.

SHORT DESCRIPTION OF THE FIGURES

FIG. 1A Space filling structure of hexacarboxyfullerene, $C_{60}(C(COOH)_2)_3$ O-3a isomer.

Figure 1C:
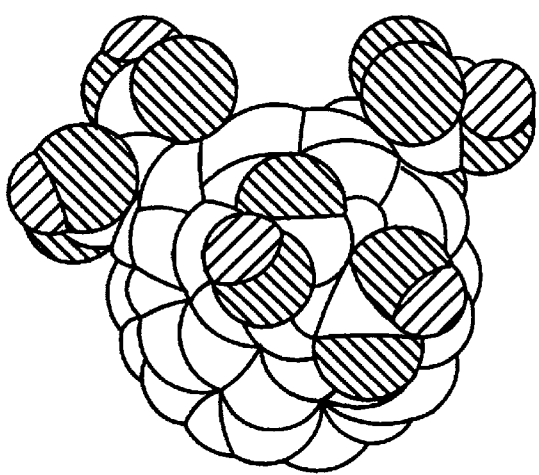
Figure 1B:
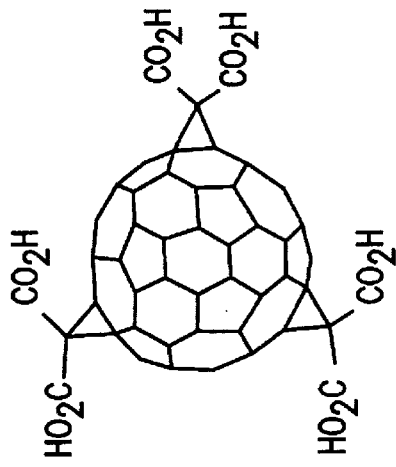

FIG. 1B Space filling structure of hexacarboxyfullerene, $C_{60}(C(COOH)_2)_3$ R-3B isomer.

FIG. 1C Chemical structure of hexacarboxyfullerene, $C_{60}(C(COOH)_2)_3$ O-3a isomer.

Figure 1D:
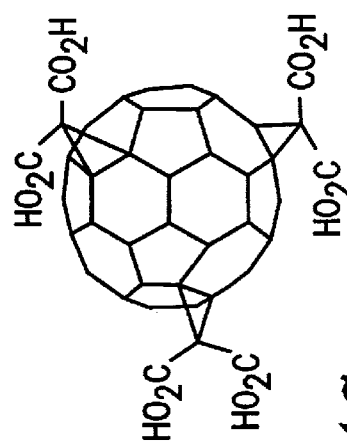

FIG. 1D Chemical structure of hexacarboxyfullerene, $C_{60}(C(COOH)_2)_3$ R-3B isomer.

FIG. 2A Spectrum of purified $C_{60}(C(COOH)_2)_3$ malonic ester (O-3a enantiomer) by proton NMR spectroscopy.

FIG. 2B Chemical structure of $C_{60}(C(CHHO)_2)_3$ malonic ester O-3a enantiomer.

Figures 3A, 3B:
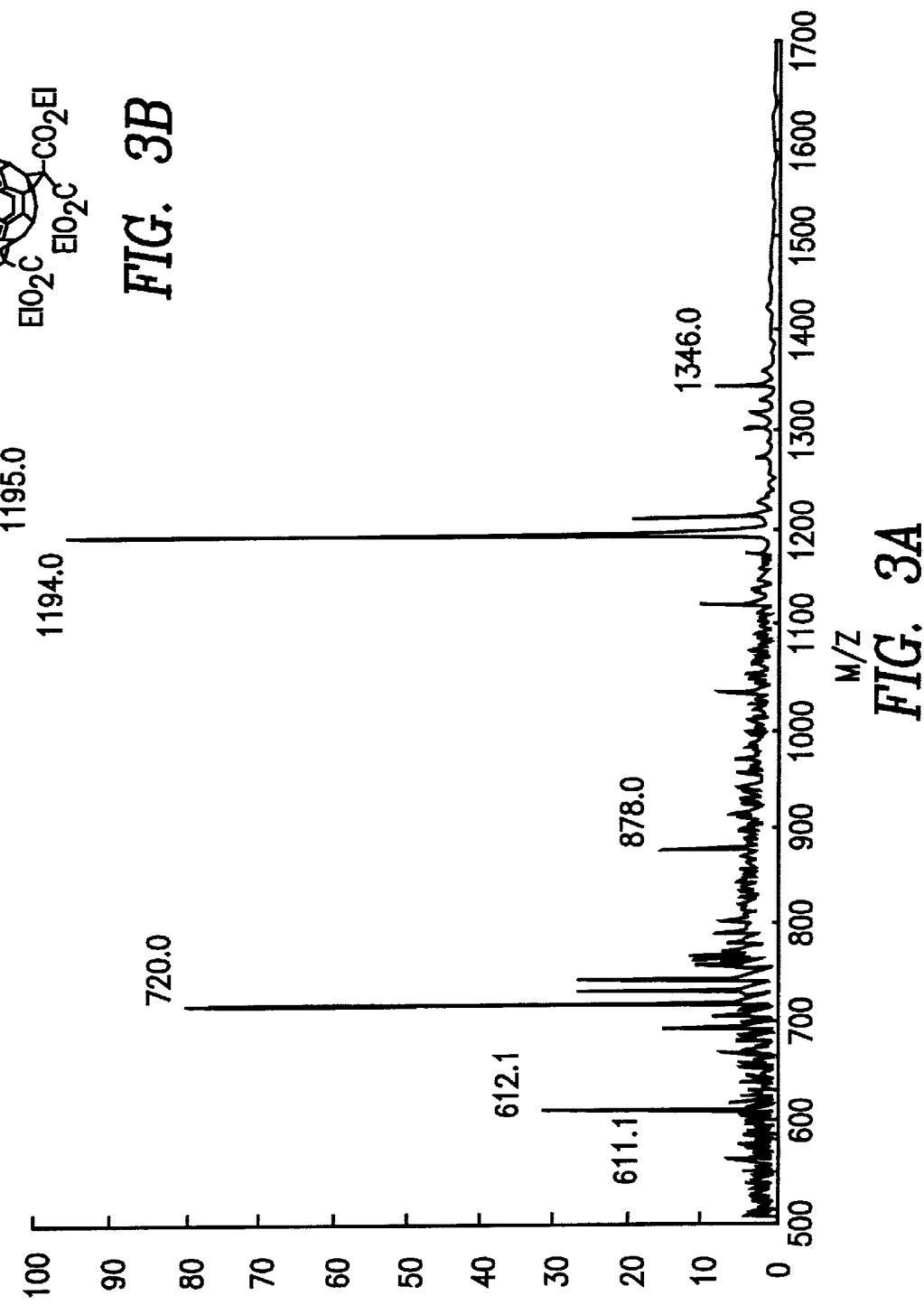

FIG. 3A Spectrum of purified $C_{60}(C(COOH)_2)_3$ malonic ester (O-3a enantiomer) by fast-atom bombardment mass spectrometry.

FIG. 3B Chemical structure of $C_{60}(C(COOH)_2)_3$ malonic ester O-3a enantiomer.

FIG. 4A–4E Electron paramagnetic resonance (EPR) spectra demonstrating the free radical activity of $C_{60}(C(COOH)_2)_3$ against $H_2O_2$ The arrows point to an artifactual signal generated by a contaminant in the EPR cavity.

FIG. 4A Hydroxyl radical generated by $H_2O_2$.

FIG. 4B Elimination of the OH signal with the introduction of O-3a isomer.

FIG. 4C Superoxide radical generated by incubating xanthine oxidase with xanthine.

FIG. 4D Elimination of superoxide radical signal with the introduction of O-3a isomer.

FIG. 4E Elimination of superoxide radical signal with the introduction of R-3B isomer.

Figure 5:
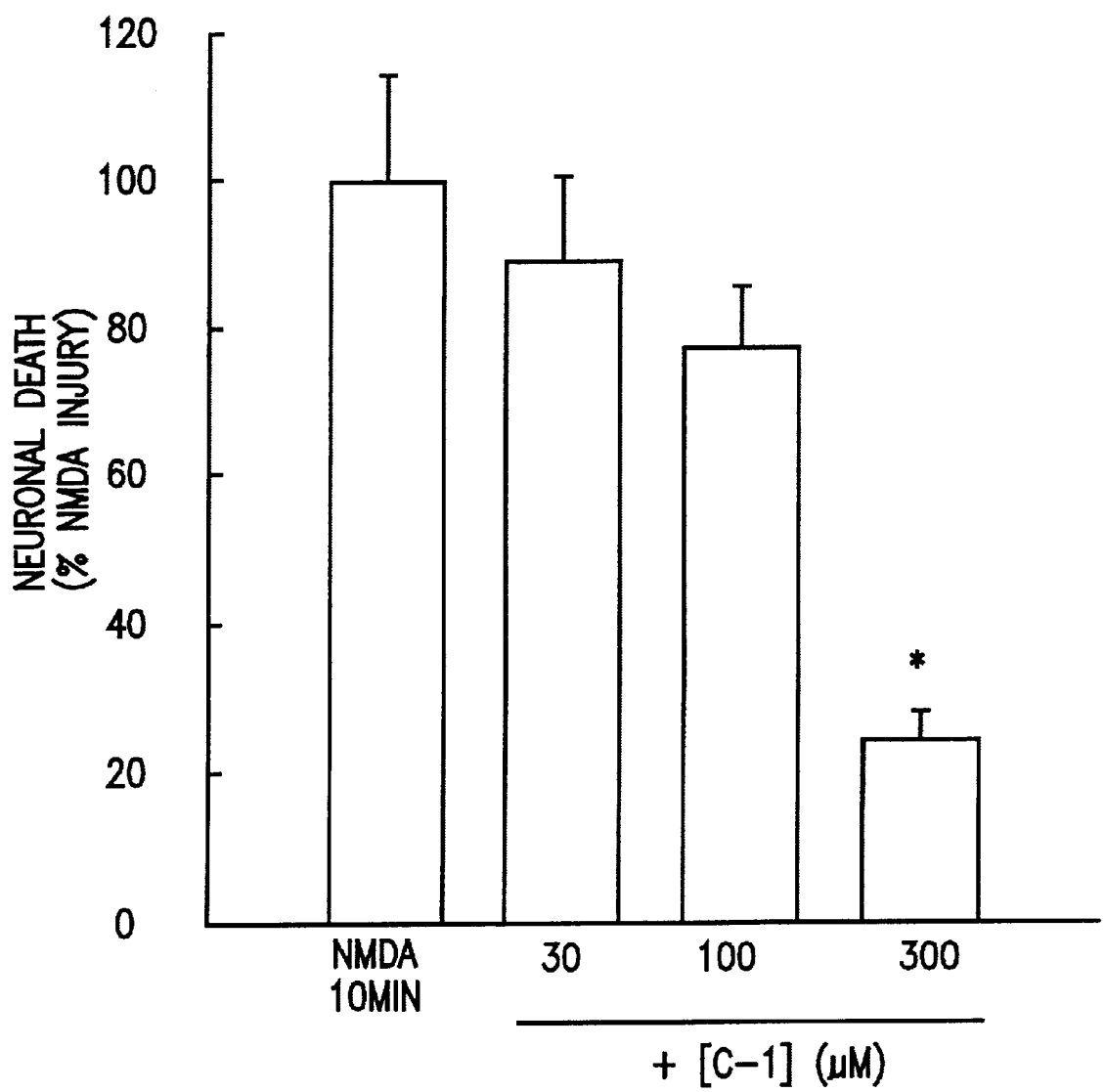

FIG. 5 Neurotoxicity produced by exposure of cultured neurons to NMDA without treatment and with three concentrations of $C_{60}(C(COOH)_2)_3$.

Figure 6:
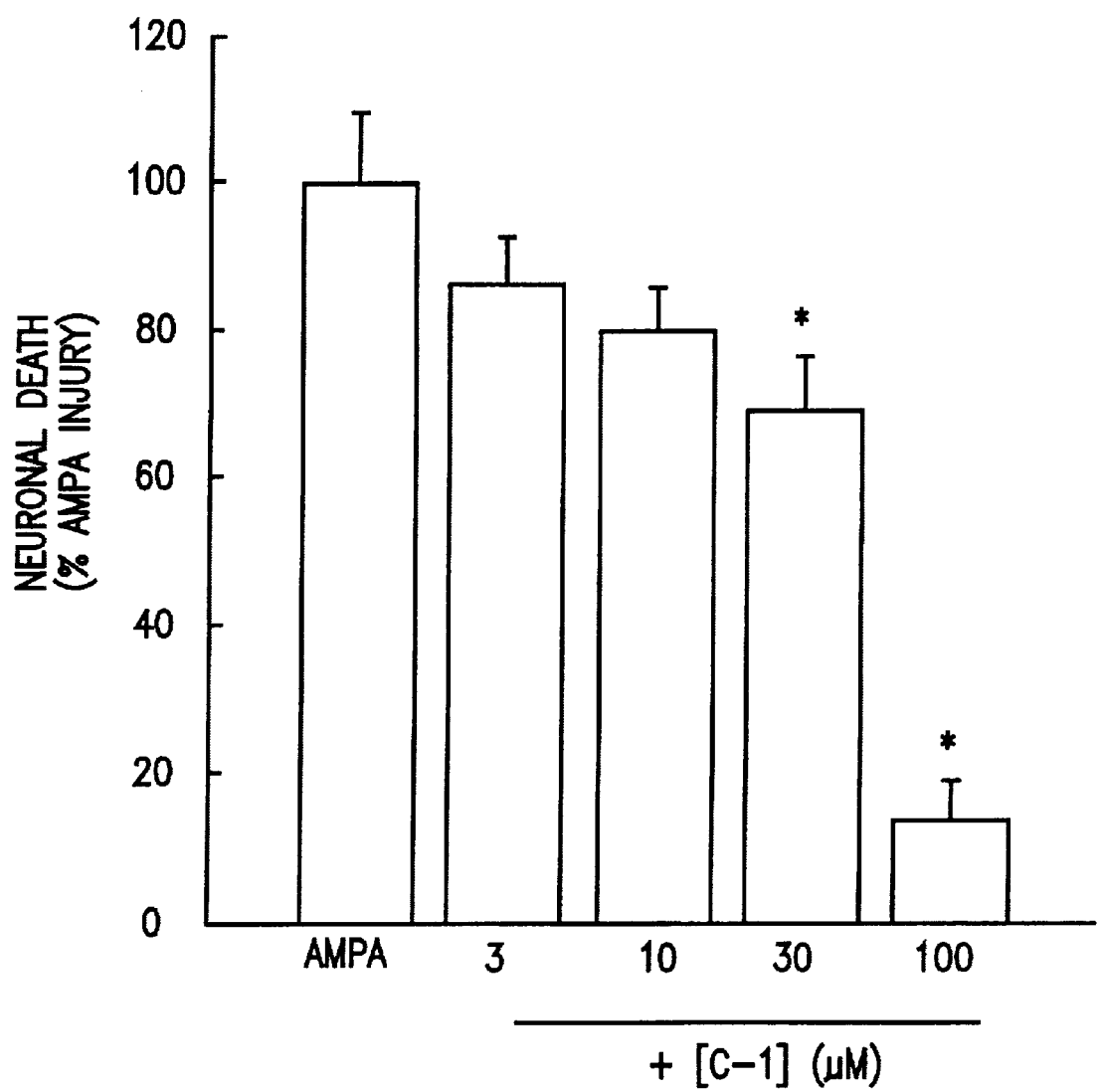

FIG. 6 Neurotoxicity produced by exposure of cultured neurons to AMPA without treatment and with four concentrations of $C_{60}(C(COOH)_2)_3$.

Figure 7:
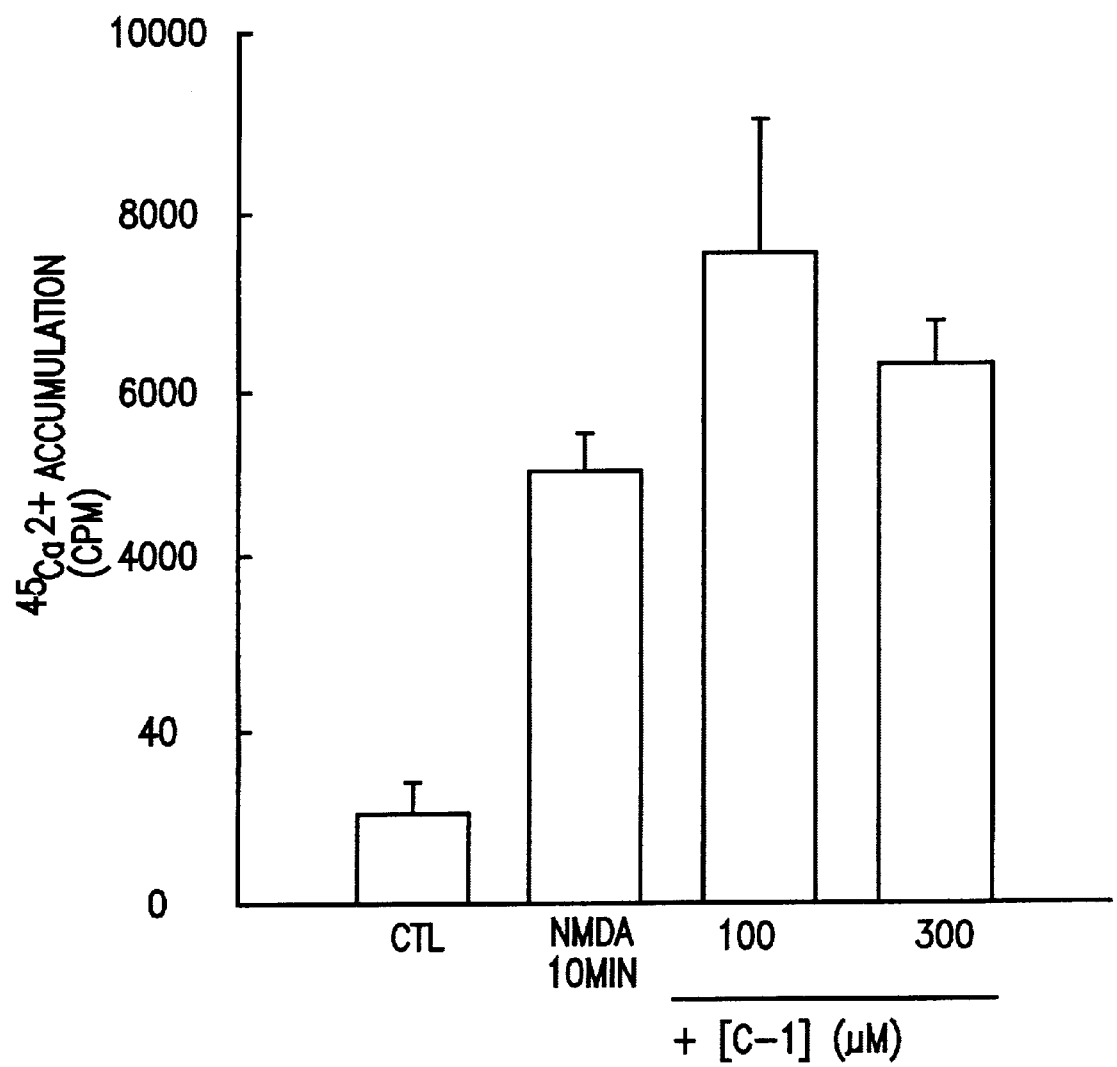

FIG. 7 NMDA-stimulated accumulation of tracer $^{45}Ca^{2+}$ in cultured neurons with and without the co-application of $C_{60}(C(COOH)_2)_3$.

Figure 8:
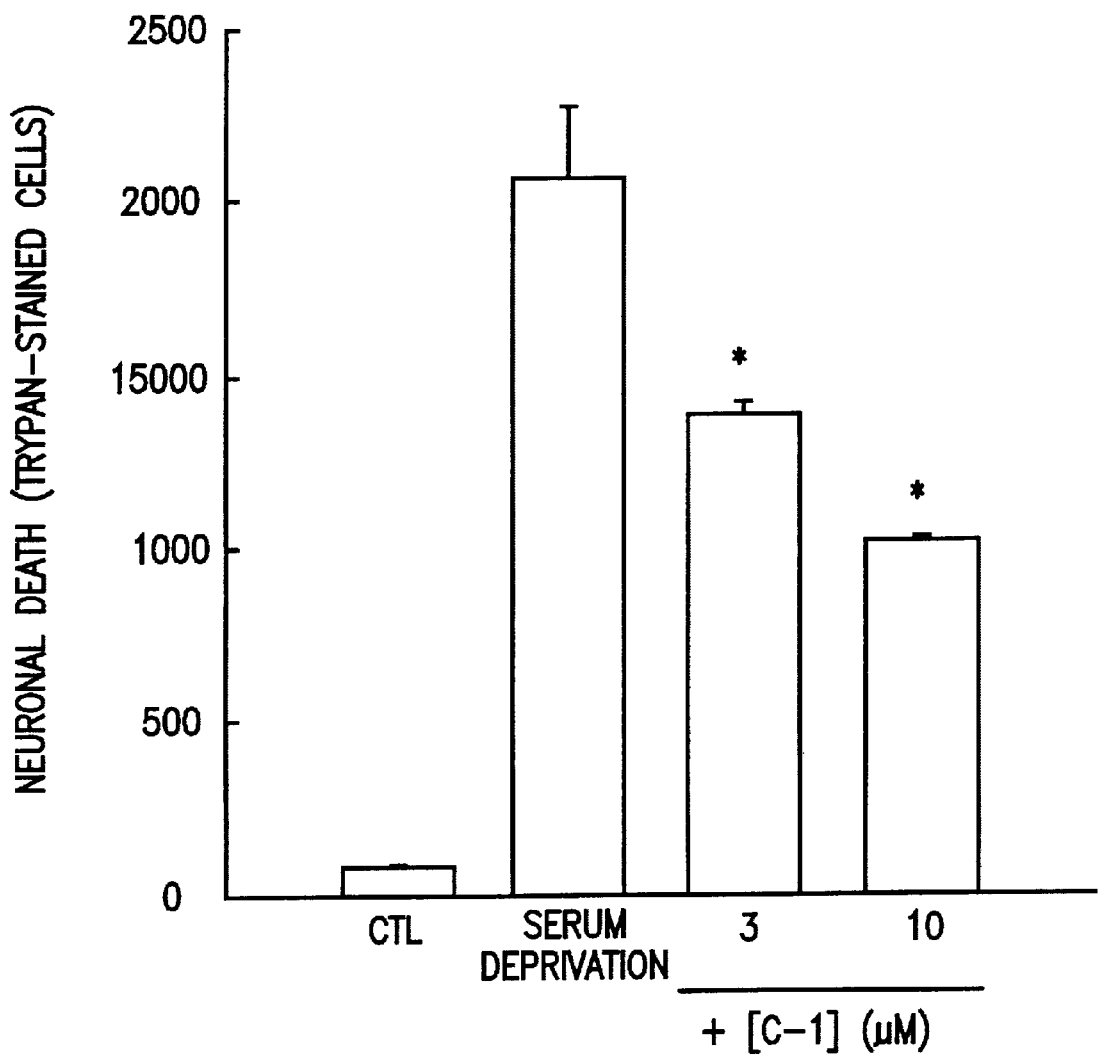

FIG. 8 Apoptotic neuronal cell death produced in glial-deficient cultures by serum deprivation without treatment and with two concentrations of $C_{60}(C(COOH)_2)_3$.

Figures 9A, 9B:
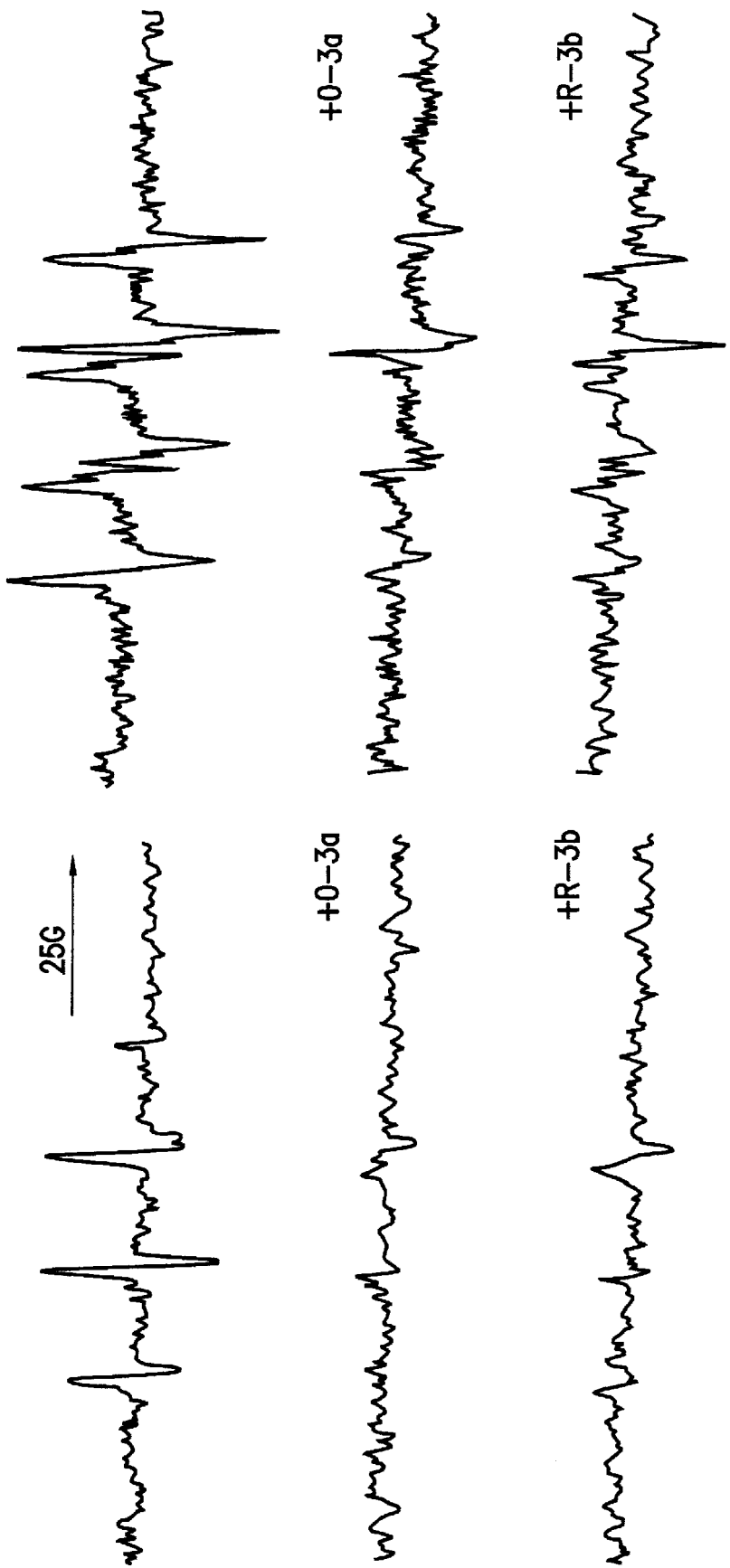

FIG. 9A EPR spectra comparing the hydroxyl radical scavenging activity of the O-3a isomer and the R-3b isomer.

FIG. 9B EPR spectra comparing the superoxide radical scavenging activity of the O-3a isomer and the R-3b isomer.

Figure 10B:
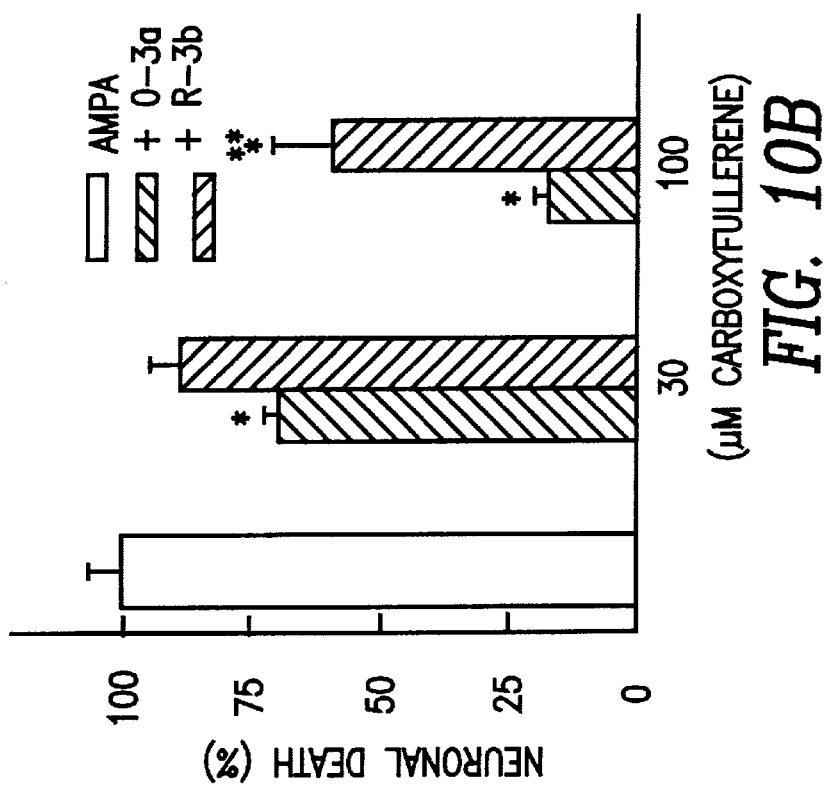
Figure 10A:
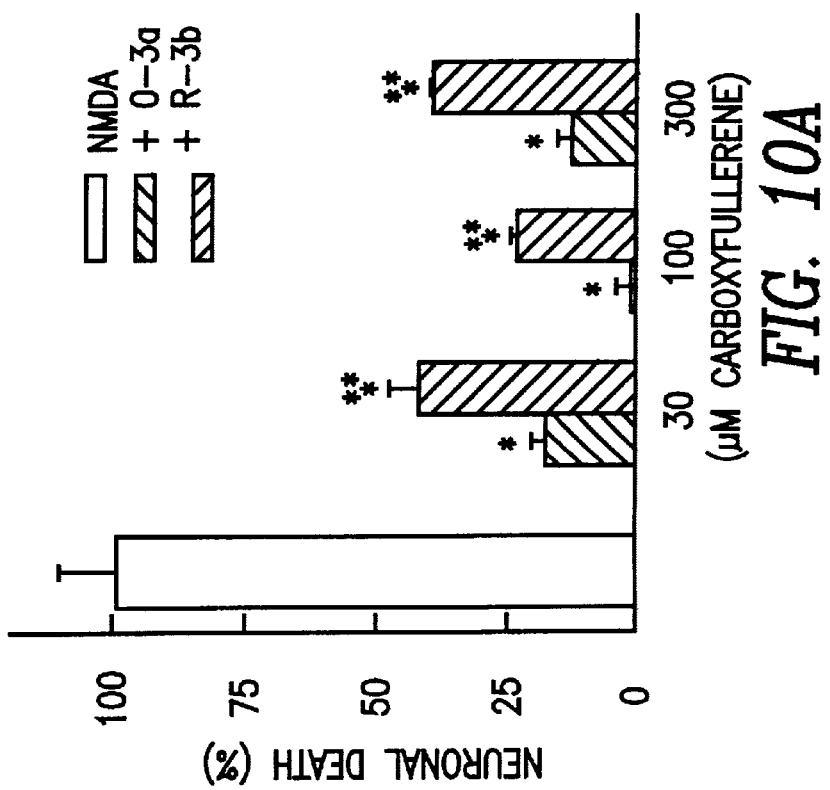

FIG. 10A Comparison of the O-3b isomers ability to protect neurons from injury produced by application of NMDA.

FIG. 10B Comparison of the O-3a isomer and the R-3b isomers ability to protect neurons from AMPA induced neuronal death.

Figure 10C:
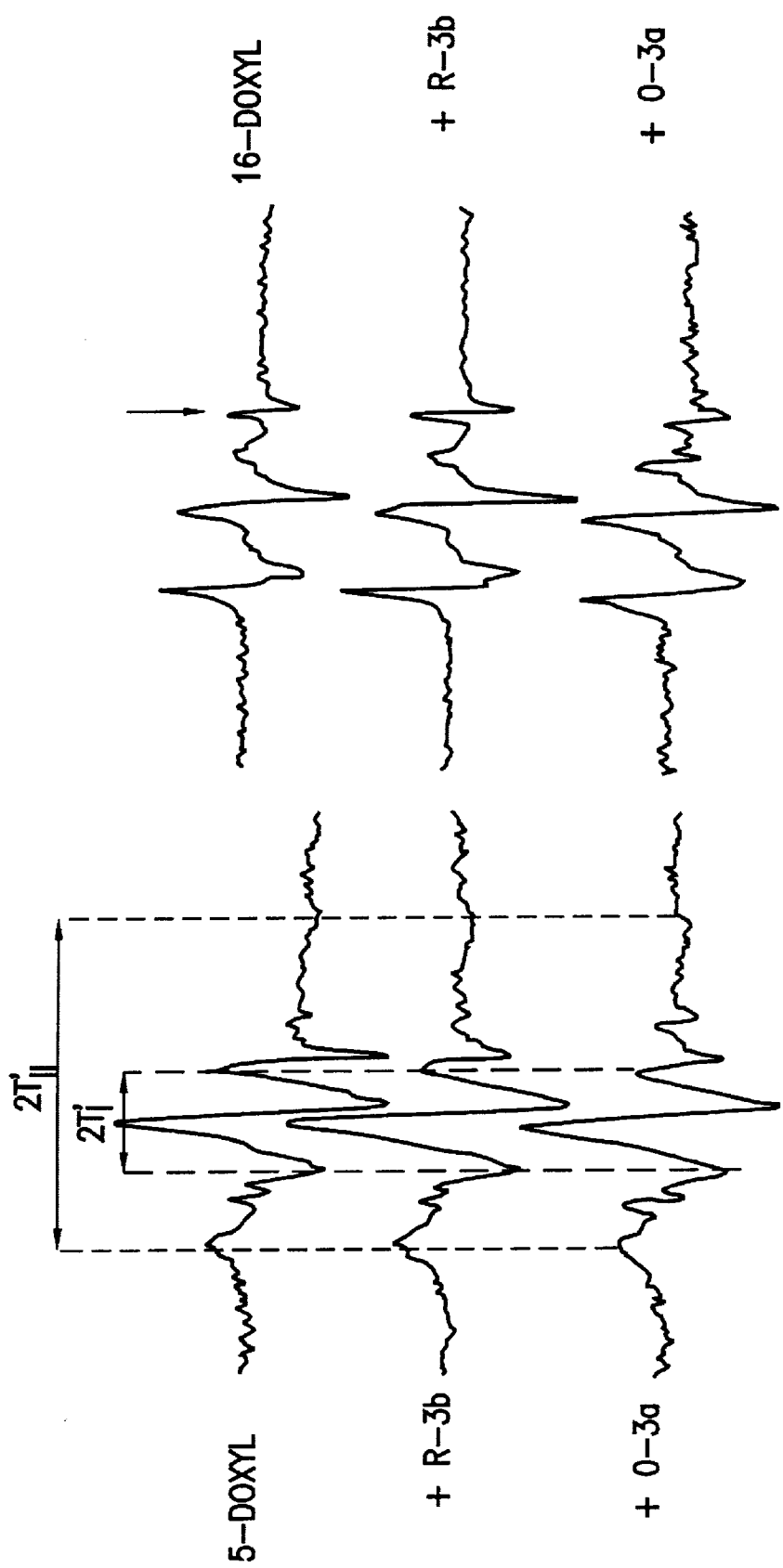

FIG. 10C EPR spectra of spin-labeled lipids (5-or 16-doxyl ketostearic acid) incorporated into lipids from mouse brain alone and in combination with the O-3a isomer and the R-3b isomer.

Figure 11:
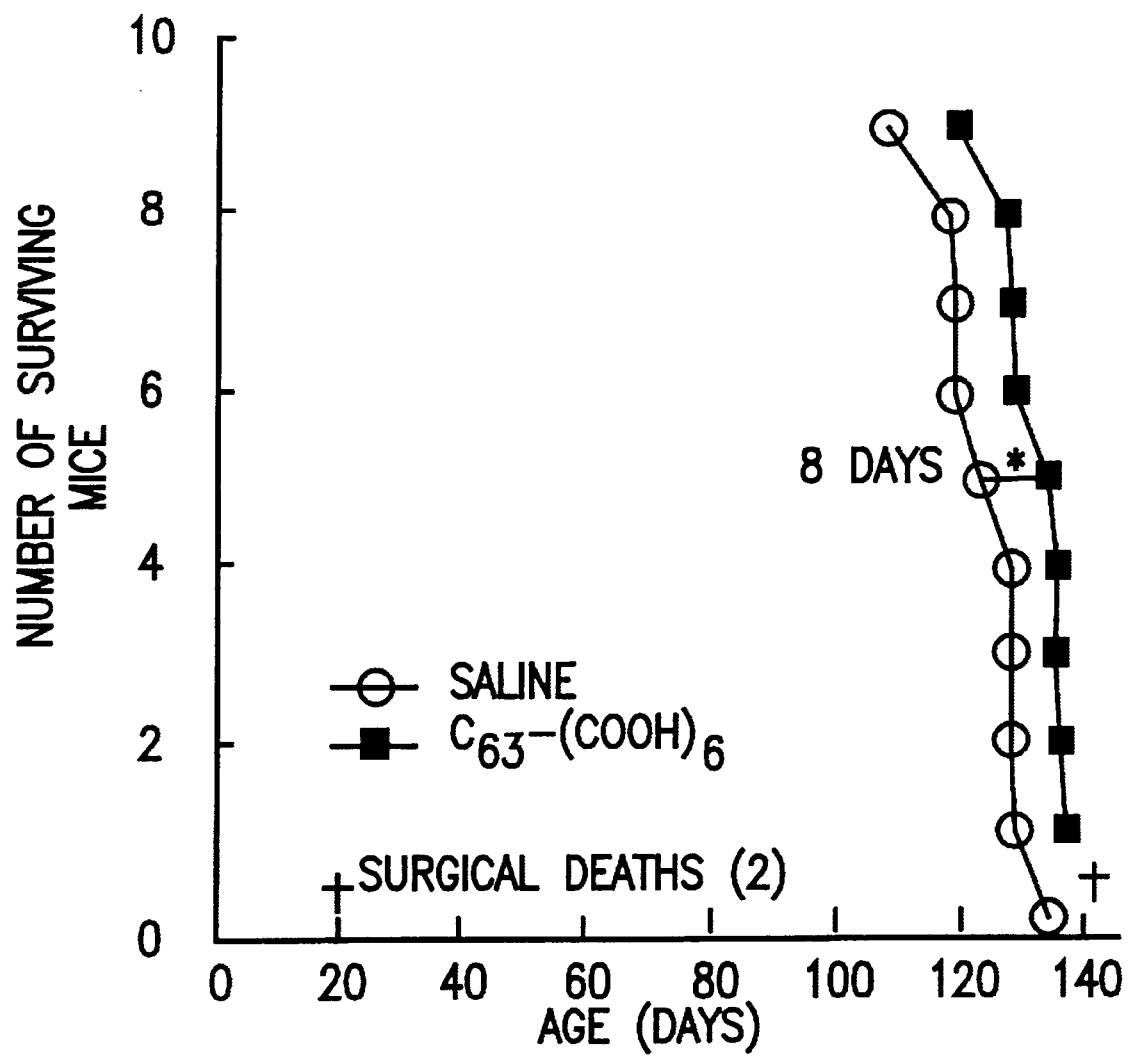

FIG. 11 Survival curves for FALS mice treated with intraperitoneal miniosmotic pumps containing saline or 15 mg/kg/day carboxyfullerene.

DETAILED DESCRIPTION OF THE INVENTION

Buckminsterfullerene, $C_{60}$, is a carbon sphere with alternating 5- and 6-carbon rings; the 30 carbon double bonds react easily with oxygen radicals (Krusic et al, 1991) and so can act as a free radical scavenger. Native $C_{60}$, however, is soluble only in a limited number of solvents, such as toluene or benzene. The compounds useful in accordance with the present invention are water soluble carboxyfullerenes, i.e., buckminsterfullerene which has been mono- or multiplideriviatized with malonic acid, or the pharmaceutically acceptable malonic acid salts, esters and amides, where the methylene group of the malonic acid is bonded to two carbons of the fullerene sphere. The compounds useful in accordance with the present invention are thus $C_{60}(C(COOH)_2)_n$ and the corresponding salts, esters and amides wherein n is an integer from 1 to 4. Examples of two isomers of $C_{60}(C(COOH)_2)_n$ where n=3 are shown in FIGS. 1A–1D. These compounds have been designated "O-3a" and "R-3b", and are the acids which correspond to the ethyl esters disclosed as compounds 3a and 3b in Hirsch et al. (1994). The preferred compounds useful in accordance with the present invention are $C_{60}(C(COOH)_2)_3$ and its pharmaceutically acceptable salts, esters and amides. The most preferred compound is the acid, itself, $C_{60}(C(COOH)_2)_3$, especially the O-3a isomer.

Thus, the present invention comprises method of treating neurotoxic injury in a patient suffering said injury by administering to said patient a composition comprising a compound of the formula $C_{60}(C(COOH)_2)_n$ where n is an integer from 1 to 4, its pharmaceutically acceptable salts, esters and amides, and a pharmaceutically acceptable carrier, wherein said compound is present in said composition in an amount effective to treat said neurotoxic injury.

The compounds useful in accordance with the invention may be used to prevent, treat or ameliorate the progression of any disease condition caused by free radicals, especially when the free radicals are released as a result of glutamate neurotoxicity. Treating neurotoxic injury within the meaning of the present invention means reducing the extent of damage to central neurons surrounding a central neuron which has released glutamate due to its having been damaged by a neurotoxic event. Neurotoxic events include acute neurological insults such as hypoxia/ischemia, such as occurs during stroke, hypoglycemia, epilepsy or trauma. Neurotoxic events may also be chronic neuronal damage caused by neurodegenerative disorders such as Huntington's disease, Alzheimer's disease, amyotropic lateral sclerosis ("ALS"), and the neurodegenerative effects of AIDS. Thus, the present invention also comprises a method of treating diseases in which said neurotoxic injury occurs.

Arachidonic acid ("AA") is released in neurons due to an influx of excessive $Ca^{2+}$ into the neuronal cells which is caused by NMDA receptor stimulation by glutamate (the glutamate having been released by neurons which were damaged by the neurotoxic event, itself). The excessive $Ca^{2+}$ influx activates phospholipase $A_2$, a calcium-dependent enzyme which breaks down cell membranes liberating the AA. The metabolism of AA by endogenous lipoxygenases and cyclooxygenases leads to the production of the oxygen free radicals that trigger peroxidative degradation of neuronal lipid membranes (Siesjo et al., 1980; Chan et al., 1985) which results in the neuronal damage or death. Therefore, in accordance with the present invention, reducing oxygen-derived free radicals by administering a composition comprising a free radical scavenging carboxyfullerene described herein provide an alternative mechanism by which glutamate-induced neurotoxicity is inhibited.

A further embodiment of the present invention is a method of inhibiting neurotoxic injury in a patient where said injury is caused by the metabolism of arachidonic acid released by neurons due to stimulation by flutamate of NMDA receptors of said neurons by administering to said patient a composition comprising a carboxyfullerene as herein described and a pharmaceutically acceptable carrier in an amount sufficient to inhibit said neurotoxic injury.

The preferred embodiment of the invention comprises a method of treating stroke by administering to a stroke patient a composition comprising a carboxyfullerene as herein described and a pharmaceutically acceptable carrier in an amount sufficient to treat said stroke. In accordance with the present invention, stroke is defined as an acute neurotoxic event in the brain of a patient wherein the neurotoxic event occurs due to a loss of blood flow to neurons of the brain.

The carboxyfullerene compounds described herein are administered systematically as a composition containing the active compound and a pharmaceutically acceptable carrier compatible with said compound. In preparing such a composition, any conventional pharmaceutically acceptable carrier may be utilized. When the drug is administered orally, it is generally administered at regular intervals.

In therapeutic use, the compounds useful in accordance with the invention may be administered by any route whereby drugs are conventionally administered. Such routes include intravenously, intramuscularly, subcutaneously, intrathecally, intraperitoneally, topically, as well as orally. Preferably, the method of the invention is carried out via oral or intravenous routes of administration.

The pharmaceutical compositions can be made up in any conventional form, including a solid form for oral administration such as tablets, capsules, pills, powders, granules, and the like. The pharmaceutical compositions may be sterilized and/or may contain adjuvants such as preservatives, stabilizers, wetting agents, emulsifiers, salts for varying the osmotic pressure, and/or buffers.

Typical preparations for intravenous administration would be sterile aqueous solutions including water/buffered solutions. Intravenous vehicles include fluid, nutrient and electrolyte replenishers. Preservatives and other additives may also be present such as antibiotics and antioxidants. Compositions for bolus i.v. administration may contain up to 10 mg/ml (10,000 mg/liter) of a carboxyfullerene described herein. Compositions for drip i.v. administration preferably contain from about 50 mg/liter to about 500 mg/liter of a carboxyfullerene described herein.

In accordance with this invention, the carboxyfullerenes described herein are useful in pharmaceutically acceptable oral modes. These pharmaceutical compositions contain said compound in association with a compatible pharmaceutically acceptable carrier material. Any conventional carrier material can be utilized. Any conventional oral dosage form such as tablets, capsules, pills, powders, granules, and the like may be used. The carrier material can be an organic or inorganic inert carrier material suitable for oral administration. Suitable carriers include water, gelatin, gum arabic, lactose, starch, magnesium stearate, talc, vegetable oils, polyalkylene-glycols, petroleum jelly and the like. Furthermore, the pharmaceutical composition may contain other pharmaceutically active agents. Additional additives such as flavoring agents, preservatives, stabilizers, emulsifying agents, buffers and the like may be added in accordance with accepted practices of pharmaceutical compounding.

A preferred oral dosage form comprises tablets, capsules of hard or soft gelatin, methylcellulose or of another suitable material easily dissolved in the digestive tract. The oral dosages contemplated in accordance with the present invention will vary in accordance with the needs of the individual patient as determined by the prescribing physician. The preferred oral dosage form is capsules or tablets containing from 50 to 500 mg of a carboxyfullerene useful in accordance with the present invention.

In carrying out the method of the invention, a compound useful in accordance with the invention is generally given to adults daily, preferably orally or intravenously, in an amount of from about 1.5 mg/kg to about 1500 mg/kg daily, in single or divided doses, preferably from about 10 mg/kg to about 60 mg/kg daily, with the precise dosage being varied depending upon the needs of the patient. In general, this therapy is carried out for a period of about three months. Alternatively, the method of the invention may be carried out prophylactically for an indefinite time in those patients who are have a high risk of suffering an acute neurotoxic event, such as a stroke. For the treatment of an acute neurotoxic event, the patient should be treated in accordance with the method of the invention as soon as possible after the diagnosis of the acute neurotoxic event, preferably within twelve hours, and most preferably within six hours, of the onset of the neurotoxic event.

The data herein demonstrates that the disclosed carboxyfullerenes are a novel class of antioxidants with the ability to scavenge multiple oxygen-derived free radicals, and that these compounds have unusual broad and powerful neuroprotective capabilities, attenuating neuronal death due to glutamate excitotoxicity, and apoptosis.

EXPERIMENTAL PROCEDURES

Solutions

Media stock (MS) consists of Eagle's Minimal Essential Media with 25 mM glucose, minus L-glutamine.

Plating medium consists of MS supplemented with L-glutamine (2 mM), 5% fetal calf serum, and 5% horse serum.

Growth medium contains MS, 10% horse serum, and 2 mM L-glutamine.

Brief exposure of NMDA is carried out in HEPES-buffered balanced salt solution, pH 7.40 (HBBSS), containing, in mM, 116 NaCl, 5.4 KCl, 0.8 MgSO$_4$, 1.8 NaPO$_4$, 12 HEPES, 25 NaHCO$_3$, 5.5 D-glucose, with 10 (M L-glucine.

Balanced salt solution (BSS) was, in mM, 116 NaCl, 5.4 KCl, 0.8 MgSO$_4$, 1.8 NaPO$_4$, 26.2 NaHCO$_3$, and 5.5 D-glucose.

The original isomer of $C_{60}(C(COOH)_2)_3$ was the O-3a isomer, which represents the major product of the synthesis. Stock of this compound was prepared as a 25 mM solution in water. Stocks were used within 72 hours of preparation, and were stored at −20° C. in the dark.

Unmodified $C_{60}$ was dissolved in toluene to make a 50 mM stock.

Cortical Cell Cultures

Mouse neocortical cultures were prepared as neuron-astrocyte co-cultures (approximately 50% astrocytes) (Rose et al., 1992) or as neuronal cultures (<2% astrocytes). Mouse embryos (gestational day 15) are removed from pregnant anesthetized Swiss-Webster mice, and the neocortex is dissected away from other brain structures. After brief incubation in trypsin, the cells are dissociated by trituration, and the cell suspension is then diluted into plating medium and plated onto previously-prepared 24-well Plastek culture plates coated with poly-D-lysine/laminin (for neuronal cultures) or onto an existing bed of astrocytes (for co-cultures). After 1–2days in vitro, a partial exchange with glial conditioned medium is made for "pure" neuronal cultures, and cytosine arabinoside (3 $\mu$M) is added immediately after feeding to inhibit glial proliferation. Mixed cultures are fed biweekly with growth medium until 11–12 days in vitro, when they are fed with serum-free MS containing 2 mM L-glutamine. Unless otherwise stated, cells were used at 14–16 days in vitro.

EXAMPLE 1

Synthesis and properties of carboxyfullerenes (2,2-fulleromalonic acids)

Diethyl 2,2-fulleromalonic ester $C_{60}$ (1 g, 1.39 mmol) was added to freshly distilled toluene (1000 ml) and stirred for a few minutes to obtain a clear, violet solution. Diethyl bromomalonate (0.474 ml, 2.78 mmol) was added dropwise to the stirred solution. Addition of 0.526 ml (3.475 mmol) DBU (1,8-diazobicyclo[5,4,0]undec-7-ene) to the fullerene solution caused the color to change from violet to dark red. After stirring overnight in air at room temperature, the solution was filtered to remove the ammonium salts, and the solvent was evaporated in varus. The residue was dissolved in a small volume of chloroform, and added to the top of a silica gel column (packing material was 70–230 mesh or 230–400 mesh flash chromatographic gel from Merck). The fullerene products were eluted using a gradient form toluene/hexane (1:1) to toluene (100%). The initial elution gave 5 fractions, unreacted fullerene, monoadducts, bisadducts, trisadducts, multiadducts. Solvent of each fraction was removed in vacuo and the solid residue was chromatographed repeatedly until pure. The fractions containing the bisadducts and the trisadducts each gave two main products on reseparation.

2,2-fulleromalonic acid(s) Samples containing single isomers of the ester adducts (100 mg) were dissolved in toluene (50 ml) under nitrogen. A 20:1 molar excess of NaH was then added. After stirring for 2–3 h at 100° C., 1 ml of methanol was added dropwise to the hot solution, producing a vigorous evolution of gas. The quantitative precipitation of sodium salt occurred concurrently. The salt was collected by centrifugation, and dried under vacuum. The dried compound was washed with 2 M $H_2SO_4$, then water. The product, representing the malonic acid derivative of the corresponding ester, was dried under vacuum overnight to give a fine brown powder.

Mass spectroscopy was performed on a sample containing the O-3a enantiomer of trisadducted fullerene ester; this ester was then hydrolyzed and acidified to form the final carboxyfullerene compound, $C_{60}(C(COOH)_2)_3$. Proton NMR and mass spectra (FIGS. 2A–2B and 3A–3B, respectively) of the purified $C_{60}$ ester indicate that the sample contains a single isomer of 2,2-fulleromalonic ester (O-enantiomer with mass=1194/1195) with a small amount of $C_{60}$ (mass=720) which may have arisen from fragmentation of the adduct. Results from the original compound, the O-3a enantiomer, are described herein. More recent studies with the other enantiomer, R-3b, indicate that it is also an effective neuroprotectant.

Solutions of carboxyfullerene were translucent brown. However, a concentrated (50 mM) solution filtered through 0.45 (m nylon filters did not leave any residue on the filters, indicating a true solution. Control experiments verified that the compounds did not interfere with the colorimetric LDH assay. Solutions of up to 25 mM of the carboxyfullerenes failed to alter the pH of the experimental solutions.

EXAMPLE 2

Excitatory amino acid toxicity and application of fullerenols

By electron paramagnetic resonance spectroscopy, $C_{60}(C(COOH)_2)_n$ compounds proved to be a potent free radical scavengers, capable of eliminating both hydroxyl and superoxide radials. FIGS. 4A through 4E show EPR spectra demonstrating the free radical scavenging activity of $C_{60}(C(COOH)_2)_3$. Spectra 4A and 4B, respectively, show the hydroxyl radical (spin adduct: DMPO-OH$^(\cdot)$) generated by $H_2O_2$ over a 15 minute period, and the elimination of this OH signal when 150 (M O-3a isomer was included with the $H_2O_2$. Superoxide radical ($O_2^{(-)}$) was also effectively scavenged by $C_{60}(C(COOH)_2)_n$ compounds. $O_2^{(-)}$, which forms the spin adduct DMPO-OOH, was generated by incubating xanthine oxidase with xanthine (Spectrum 4C). Co-incubation with either 40 (M O-3a isomer or 40 (M R-3b eliminated the superoxide radical signal (Spectra 4D and 4E, respectively). EPR analysis of other water-soluble $C_{60}(C(COOH)_2)_n$ compounds with n=1 or 2 confirmed that they were also effective free radical scavengers (data not shown).

The hexacarboxylated compound, $C_{60}(C(COOH)_2)_3$, which was soluble in water to at least 50 mM, protected cortical neurons against excitotoxic injury produced by exposure to N-methyl-D-aspartate (NMDS) and (-amino-3-hydroxy-5-methyl-4-isoxazole propionic acid (AMPA). The dicarboxy and tetracarboxy fullerene derivatives were less soluble in aqueous solution and, while possessing neuroprotective activity, were less effective neuroprotectants than the hexacarboxy derivative.

Carboxyfullerene (3–300 (M) was co-applied to neuron-astrocyte co-cultures described above with NMDA for assessment of neuroprotection. Brief exposure to NMDA in the presence of the carboxyfullerene was carried out by triple exchange of the medium with HBBSS, followed by addition of 50 µM–500 µM NMDA plus carboxyfullerene for 10 minutes. The NMDA and carboxyfullerene were removed by quadruple exchange of the medium with MS, and the cultures were placed in the humidified, $CO_2$ (5%), 37° C. incubator for 24 hours, when the extent of injury was assessed.

Prolonged (24 hours) exposure to 5–100 (M AMPA is routinely used to produce cortical neuronal injury. In another series of experiments, carboxyfulerene (3–300 (M) was co-applied to neuron-astrocyte co-cultures described above, with AMPA, for assessment of neuroprotection. After the medium was exchanged twice with MS, AMPA and carboxyfullerene were added and cultures were returned to the 37° C. incubator. The NMDA receptor antagonist, MK-801 (10 (M) was included with the AMPA and carboxyfullerene to eliminate secondary activation of NMDA receptors by endogenous glutamate release.

Neuronal death was assessed at 24 hours after NMDA or AMPA administration by phase contrast microscopy at 200–400x, and by measurement of lactate dehydrogenase (LDH) efflux from dying cells into the bathing medium (Koh and Choi, 1987). Quantitation of cell death was confirmed in some experiments by trypan blue or propidium iodide staining and cell counting.

Results for $C_{60}(C(COOH)_2)_3$ are shown in FIGS. 5 and 6. $C_{60}(C(COOH)_2)_3$ showed robust neuroprotection against NMDA (FIG. 5) and AMPA-induced (FIG. 6) excitotoxic neuronal injury. $C_{60}(C(COOH)_2)_3$ (300 (M) reduced neuronal death from NMDA by at least 60% in all experiments performed to date, and afforded nearly complete protection in some experiments. The amount of LDH present in washed controls was subtracted to give the signal specific to NMDA toxicity. Data are graphed as the percentage of cell death produced by NMDA alone: this exposure killed 51 ( 9, 44 ( 6, and 88 ( 14 % of the total neurons per culture. mean ( S.D. *=p<0.05 vs. NMDA, by ANOVA followed by Student-Newman-Keuls test for multiple comparisons. Pooled data from three experiments (FIG. 5) demonstrate a 75% reduction in neuronal cell death.

$C_{60}(C(COOH)_2)_3$ reduced neuronal cell death from AMPA by >80% at 100 (M (FIG. 6). MK-801 (10 (M) was included with AMPA to eliminate secondary activation of NMDA receptors by released endogenous glutamate. Values are mean ( SEM, n=3–4/experiment, data from 4 experiments are pooled. Data are graphed as the percentage of cell death produced by AMPA/MK-801 alone, representing 40–70% of the total neurons/culture. *=p<0.05 vs. AMPA, by ANOVA followed by Student-Newman-Keuls test for multiple comparisons.

The experiments described here are, to our knowledge, the first use of these compounds as cytoprotective agents or as antioxidants.

EXAMPLE 3

$^{45}Ca^{2+}$ tracer experiments

To verify that protection against NMDA-induced neuronal cell injury was not due to a reduction in NMDA-induced calcium influx, $^{45}Ca^{2+}$ tracer studies were performed. Cultures were washed twice with HBBSS and then exposed to NMDA (300 (M), either alone or with $C_{60}(C(COOH)_2)_3$, in HBBSS containing tracer $^{45}Ca^{2+}$ (0.5 (Ci/culture well; NEN, Boston, Mass.). The exposure was terminated after 10 minutes by exchanging the medium four times with unlabelled HBBSS, followed by lysis of the cells by addition of 0.2% sodium dodecyl sulfate (SDS). The cells were left in SDS for 2 hours, and the lysate was then transferred to scintillation vials. An additional wash of each culture well with SDS was added to the vial, which then underwent (-counting.

The results in FIG. 7 demonstrate that the carboxyfullerenes are not NMDA receptor antagonists. $^{45}Ca^{2+}$ accumulation was not affected by co-application of up to 300 (M of $C_{60}(C(COOH)_2)_3$ with NMDA. Basal $^{45}Ca^{2+}$ was subtracted from all conditions to give the $^{45}Ca^{2+}$ increase specific to NMDA receptor activation. Mean ( SEM, n=4.

EXAMPLE 4

Serum deprivation apoptotic neuronal death

Cortical neurons in glia-deficient culture undergo apoptotic cell death 24–48 hours after removal of serum, as characterized by morphologic changes such as cell body shrinkage, fragmentation of neuronal processes, and chromatin condensation by Hoechst 33258 staining (Dugan et al, 1995). Apoptotic neuronal death due to serum deprivation was also attenuated by co-application of hexacarboxyfullerene. This injury has been shown to have features typical of apoptosis, including DNA laddering, chromatin clumping, cell shrinkage, formation of apoptotic bodies, and protection by macromolecular synthesis inhibitors. Cortical neurons in cultures containing less than 1% astrocytes were deprived of serum by exchanging the serum-containing growth medium with a balanced salt solution supplemented with amino acids (excluding glutamine). Washed controls were returned to medium containing 2% fetal calf serum, 2% horse serum in BSS. After 24 and 48 hours, the cells were photographed using phase contrast optics at 100–400×, using a Nikon inverted microscope.

Additionally, neuronal cell death was determined at 48 hours removal of serum by counting cells that are no longer able to exclude trypan blue. As shown in FIG. 8, neuronal cell death, determined at 48 hours after the onset of serum-deprivation by counting cells that were no longer able to exclude trypan blue, demonstrated a significant reduction in neuronal death. Cells treated with 10 (M $C_{60}(C(COOH)_2)_3$ demonstrated a 50% reduction in neuronal death. Washed control cultures maintained in serum-containing medium had very little death. Values are mean ( SEM, n=3–4/experiment. This experiment is representative of 3 experiments. *=p<0.05 vs. serum-deprivation, by ANOVA followed by Student-Newman-Keuls test for multiple comparisons.

EXAMPLE 5

Polar location of carboxyl groups on $C_{60}$ improves neuroprotective efficacy

Two regioisomers of $C_{60}(C(COOH)_2)_3$, O-3a and R-3b, were synthesized and purified following the method of Lamparth and Hirsch (Lamparth and Hirsch (1990)). The purity of these compounds was verified by NMR and UV/Visible spectral analyses. In the O-3a compound, all methano bridges are in e(quatorial) positions relative to each other (e,e,e), and the molecule has $C_3$ symmetry as demonstrated by $^1H$ and $^{13}C$ NMR spectroscopy. Compound R-3b has methano bridges which lie on a belt along the equator about the threefold axis of the $C_{60}$ framework in trans-3 positions (trans-3, trans-3, trans-3), and has $D_3$ symmetry. The 3-D structures shown in FIG. 1 illustrate the polar distribution of the carboxyl groups on O-3a and the equatorial distribution of the carboxyl groups on R-3b.

FIGS. 9A and 9B show that, chemically, these two isomers showed similar abilities to scavenge OH and $O_2$-free radicals, as judged from spin-trap/EPR spectra. FIGS. 9A and 9B show the EPR spectra of OH (from 100 μM $H_2O_2$ in $Fe^{2+}$ by the Fenton reaction) and $O_2$- (from xanthine+xanthine oxidase) radicals with 100 mM 5,5-dimethyl-1-pyrolline-N-oxide (DMPO) as the spin-trapping agent. Hydroxyl radical (FIG. 9A): OH in the presence of IMPO alone (top), in the presence of 4 mM O-3a (middle), or in the presence of 4 mM R-3b (bottom). Superoxide radical (right): $O_2$- in DMPO alone (top), in the presence of 400 mM O-3a (middle), in the presence of 400 mM R-3b (bottom). The arrow designates a spurious signal due to an unknown radical in the cavity. The sample was analyzed in a quartz flat cell (60×10×0.25 mm) in a Bruker 200, X-band EPR spectrometer. Settings were power=1.6 mW, modulation=1 G, field modulation=100 Hz, R.G.=3.2×10$^5$.

The EPR results demonstrate that both O-3a and R-3b isomers are extremely potent scavengers of OH at concentrations 100 to 1000-fold less than reported for most other free radical scavengers. The scavenging ability of carboxyfullerene towards OH is 10-fold greater than than its potency for $O_2$-radicals.

Although the O-3a and R-3b isomers are equipotent anti-oxidants by EPR analysis, the O-3a compound was biologically more effective than R-3b against both NMDA and AMPA receptor-mediated injuries. These results are shown in FIGS. 10A, 10B and 10C. FIGS. 10A, 10B and 10C demonstrate that O-3a provided slightly better protection from injury produced by application of NMDA FIG. 10A, but substantially better protection against AMPA-induced neuronal death FIG. 10B. Values are mean±SEM, n=8–12 per condition. I=p<0.05 vs. untreated injury condition, using ANOVA followed by Student-Newman-Keuls test for multiple comparisons. **=p<0.05 R-3b different than O-3a. FIG. 10C also shows the EPR spectra of spin-labeled lipids (5- or 16-doxyl ketostearic acid) incorporated into lipids from mouse brain, plus either O-3a or R-3b. The spin labels were added to lipids extracted from adult mouse brain at a ratio of 1:100. EPR settings were the same as those listed in the legend for FIGS. 9A and 9B. Both isomers produce a shift in the order parameter (S) of the 5-doxyl group, but O-3a produced a greater change in S (Table 1). O-3a also altered the liquid state signal from 16-doxyl ketostearic acid to a greater extent than R-3b, indicating that O-3a increased the disorder, or fluidity, of the lipids (Table 1). Both results suggest that O-3a enters the lipid bilayer to a greater extent than R-3b.

In addition to its greater activity in protecting neurons from NMDA and AMPA receptor-mediated injuries, O-3a provided enhanced protection over R-3b from such injury in endothelial cell cultures and in hepatocytes. This difference was apparently due to the ability of the O-3a isomer to enter membranes to a greater extent than R-3b. The polarity of O-3a enables it to enter the cell membrane more easily. This ability to intercalate into membranes suggests that O-3a would provide better protection of cell membranes from lipid peroxidation than R-3b. Thus, the location of functional groups (polar vs. circumferential) is important for the protective efficacy of $C_{60}$ derivatives.

TABLE 1

Membrane parameters from spin-label/EPR experiments

| Compound | Order parameter[a] | Correlation time[b] | Lipid/aqueous partition factors[c] |
|---|---|---|---|
| O-3a | 0.84 ± 0.01 | 5.7 ± 0.5 ns | 1.0 ± 0.2 |
| R-3b | 0.86 | 4.5 | 0.6 |
| Control | 0.88 | 5.1 | 0.8 |

[a]Order parameter, S = a(T_¢ − T . ¢)/(T − T .), where T_¢ is the measured hyperfine splitting for the parallel orientation in 5-doxylstearic acid spin label/phospholipids, and T . ¢ the perpendicular orientation. We assume a = 1, and T − T . = 25 G.
[b]Correlation time, $t_c = 6.5 \times 10^{-10} w_o [(h_o/h_{-1})^- -1]$, where $w_o$ is the width of the mid-field line in gauss, $h_o$ and $h_{-1}$ are peak height of mid- and high-field lines on the first derivative absorption measured for 5-doxylstearic acid.
[c]Lipid/aqueous partition factor, $f = h_L/h_A$, where $h_L$ and $h_A$ are the peak height of lipid and aqueous phases measured for 16-doxylstearic acid. We used ½ of the full height of $h_A$ for valid comparison.

EXAMPLE 6

Effect of Carboxyfullerenes on Survival in a Transgenic Model of Amyotrophic Lateral Sclerosis One in 10,000 individuals develop ALS, the most common cause of death due to motor neuron disease. The familial form of the disease (FALS) is usually autosomal dominant, constituting 10–15% of cases. In 1993, a critical breakthrough identified mutations in the Cu,Zn-SOD (sod1) gene in certain families with FALS (Rosen et al., 1993), and subsequent work has lead to the hypothesis that ALS may be due to enhanced production of reactive oxygen species (ROS) by mutant SOD1 in some forms of FALS.

Gurney and colleagues have developed mice bearing the $G^{93}A$ point mutation found in FALS families (Gurney et al, 1994), and the G1 line of $G^{93}A$ transgenic mice demonstrate many of the features of human FALS. The G1 line, with 18 copies and 4 times the SOD activity of wildtype animals, develops motor neuron death by 3–4 months of age, with hindlimb weakness, impaired grooming, and thinning along their flanks. Affected mice were dead before 5 months of age (Gurney et al., 1994).

$C_{60}(C(COOH)_2)_3$ was used to treat FALS mice (Gurney G1 strain) to determine its ability to treat FALS. At 10 weeks of age, Alzet mini-osmotic pumps (28 day, 6 (l/day, 15 mg/kg/day) containing $C_{60}(C(COOH)_2)_3$ (the mixed isomers, which consist of >90% O-3a) or saline were implanted intraperitoneally. The pumps were replaced at 14 weeks of age. Videotaped assessments of open field walking were performed and scored using the Bresnahan scale for spinal cord injury (Basso et al, 1995). As reported by Gurney and colleagues, these animals develop motor symptoms by approximately 90 days of age, and are moribund between 125 and 145 days of age.

FIG. 11 shows the survival curves for FALS mice treated with intraperitoneal mini-osmotic pumps containing saline or 15 mg/kg/day carboxyfullerene. These results demonstrate that the group treated with $C_{60}(C(COOH)_2)_3$ showed an 8±2.2 day delay in death, p=0.041 by t-test. The FALS mice treated with $C_{60}(C(COOH)_2)_3$ also demonstrated a delay in onset of symptoms. The 8 day increase in survival reached statistical significance (p=0.041), by t-test. There was no difference in survival for FALS mice who received no pumps (123 days, n=4) or those treated with saline-filled pumps (125 days, n=6). In addition, wild-type animals (n=6) treated two months with carboxyfullerene (15/mg/kg/day) showed no adverse health or behavioral effects—they were as active as untreated littermates, and weights were similar (within genders).

REFERENCES

Basso, D. M., Beattie, M. S. and Bresnahan, J. C. (1995) A sensitive and reliable locomotor rating scale for open field testing in rats. *J. Neurotrauma* 12:1–21.

Beal, M. F. (1992). Does impairment of energy metabolism result in excitotoxic neuronal death in neurodegenerative illness? *Ann. Neurol.* 31: 119–130.

Braughler, J. M. and Hall, E. D. (1989) Central nervous system trauma and stroke. I. Biochemical considerations for oxygen radical formation and lipid peroxidation. *Free. Radic. Biol. Med.* 6:289–301.

Bruno, V., Battaglia, G., Copani, A., Sortino, M. A., Canonico, P. L., and Nicoletti, F. (1994) Protective action of idebenone against excitotoxic degeneration in cultured cortical neurons. *Neurosci. Lett.* 178:193–196.

Chan, P. H., Fishman, R. A., Longar, S., Chen, Yu, A. (1985) Cellular and molecular effects of polyunsaturated fatty acids in brain ischemia and injury. *Prog. Brain Res.* 63:227–235.

Chan, P. H., Chu, L., Chen, S. F., Carlson, E. J., Epstein, C. J. (1990) Attenuation of glutamate-induced neuronal swelling and toxicity in transgenic mice overexpressing human CuZn-superoxide dismutase. *Acta Neurochirurgica.* 51:245–247.

Chan, P. H., Yand, G. Y., Chen, S. F., Carlson, E. Epstein, C. J. (1991) Cold-induced brain edema and infarction are reduced in transgenic mice overexpressing CuZn-superoxide dismutase. *Ann. Neurol.* 29:482–486.

Choi, D. W. (1988) Glutamate neurotoxicity and diseases of the nervous system. *Neuron* 1:623–634.

Chow, H. S., Lynch, J. L., Rose, K., and D. W. Choi, D. W. (1994) Trolox attenuates cortical neuronal injury induced by iron, ultraviolet light, glucose deprivation, or AMPA. *Brain Res.* 639:102–108.

Coyle, J. T. and Puttfarcken, P. (1993) Oxidative stress, glutamate, and neurodegenerative disorders. *Science* 262:689–694.

Dessi, F., Moreau, J., Lasbennes, F., Ben-Ari, Y., and Charriaut-Marlangue, C. (1993) Regional variability in DNA fragmentation after global ischemia evidenced by combined histological and gel electrophoresis observations in the rat brain. *J. Neurochem.* 61:1973–1976.

Dugan, L. L., Bruno, V. M. G., Amagasu, S. M., and R. G. Giffard, R. G. (1995) Glia modulate the response of murine cortical neurons to excitotoxicity: glia exacerbate AMPA neurotoxicity. *J. Neurosci.* 15:4545–4555.

Dugan, L. L., Bruno, V. M. G., Amagasu, S. M., Choi, D. W. and Giffard, R. G. (1992) NMDA receptor activation results in hydroxyl radical production in primary murine cortical cultures. *Soc. Neurosci. Abs.* 18:756.

Dukens, J. A., Stern, A., and Trenkner, E. (1987) Mechanism of kainate toxicity to cerebellar granule neurons in vitro is analogous to reperfusion tissue injury. *J. Neurochem.* 49:1222–1228.

Faden, A. I. and Simon, R. P. (1988) A potential role for excitotoxins in the pathophysiology of spinal cord injury. *Ann. Neurol.* 23:623–626.

Flamm, E. S., Demopoulos, H. B., Seligman, M. L., Poser, R. G., and Ransohoff, J. (1978) Free radicals in cerebral ischemia. *Stroke* 9:445–447.

Franklin, J. L., Miller, T. M., and Johnson, E. M. (1994) Inhibition of programed cell death by spin traps:evidence of a role for reactive oxygen in neuronal apoptosis. *Soc. Neurosci. Abs.* 20:432.

Goldberg M. P. and D. W. Choi. (1993) Combined oxygen and glucose deprivation in cortical culture: calcium-dependent and calcium-independent mechanisms of neuronal injury. *J. Neurosci.* 13:3510–3524.

Greenamyre, J. Y., Penney, J. B., Young, A. B., D'Amato, C. J., Hicks, S. P., and Shoulson, I. (1985) Alterations in L-glutamate binding in Alzheimer's and Huntington's diseases. *Science* 227:1496–1498.

Griffiths, T., Evans, M. C., Meldrum, B. S. (1984) Status epilepticus: the reversibility of calcium loading and acute neuronal pathological changes in the rat hippocampus. *Neurosci.* 12:557–567.

Gurney, M. E., Haifeng, P., Chiu, A. Y., Dal Canto, M. C., Polchow, C. Y. et al (1994) Motor neuron degeneration in mice that express a human Cu, Zn superoxide dismutase mutation. *Science* 264: 1772–1775.

Gurney, M. E., Cuttings, F. B., Zhai, P., Doble, A., Taylor, C. P., Andrus, P. K., and Hall, E. D. (1996) Benefit of vitamin E, riluzole, and gabapentin in a transgenic model of amyotrophic lateral sclerosis. *Ann. Neurol.* 39:147–157.

Halliwell, B. (1992) Reactive oxygen species and the central nervous system. *J. Neurochem.* 59:1609–1623.

Hirsch, A., Lamparth, I. and Karfunkel, H. R. (1994) Fullerene Chemistry in Three Dimensions: Isolation of seven regiosomeric bisadducts and chiral trisadducts of $C_{60}$ and di(ethoxy carbonyl) methylene. *Angew. Chem. Int. Ed. Engl.* 33: 437–438.

Hockenbery, D. M., Oltvai, Z. N., Yin, X. M., Milliman, C. L., and Korsmeyer, S. J. (1993) Bcl-2 functions in an antioxidant pathway to prevent apoptosis. *Cell* 75:241–251.

Imaizumi, S., Woolworth, V., Fishman, R. A., and Chan, P. H. (1990) Liposome-entrapped superoxide dismutase reduces cerebral infarction in cerebral ischemis in rats. *Stroke* 21:1312–1317.

Kinouchi, H., Epstein, C. J., Mizui, T., Carlson, E., Chen, S. F., Chan, P. H. (1991) Attenuation of focal cerebral ischemic injury in transgenic mice overexpressing CuZn superoxide dismutase. *Proc. Natl. Acad. Sci. U.S.A.* 88:11158–11162.

Koh, J., and Choi, D. W. (1987) Quantitative determination of glutamate mediated cortical neuronal injury in cell culture by lactate dehydrogenase efflux assay. *J. Neurosci. Meth.* 20:83–90.

Kontos, H. A. and Wei, E. P. (1986) Superoxide production in experimental brain injury. *J. Neurosurg.* 64:803–807.

Krusic, P. J. Wasserman, E., Keizer, P. N. Morton, and J. R. Preston, K. F. (1991) Radical reactions of $C_{60}$. *Science* 254: 1183–1185.

Lafon-Cazal, M., Pietri, S., Calcasi, M., and Bockaert, J. (1993) NMDA-dependent superoxide production and neurotoxicity. *Nature* 364:535–537.

Lamparth, I., Hirsch, A. (1990) *J. Chem. Soc., Chem. Commun.* 1994:1727.

Lesiuk, H., Sutherland, G., Peeling, J., Butler, K., Saunders. (1991) Effect of U74006F on forebrain ischemia in rats. *Stroke* 22:896–901.

Liu, T. H., Beckman, J. S., Freeman, B. A., Hogan, E. L., Hsu, C. Y. (1989) Polyethylene glycol-conjugated superoxide dismutase and catalase reduce ischemic brain injury. *Amer. J. Physiol.* 256:H589–93.

MacManus, J. P., Hill, I. E., Huang, Z. G., Rasquinha, I., Xue, D., and Buchan, A. M. (1994) DNA damage consistent with apoptosis in transient focal ischaemic neocortex. *Neuroreport* 5:493–496.

Meldrum, B. (1985) Possible therapeutic applications of antagonists of excitatory amino acid transmitters. *Clin. Sci.* 68:113–122.

Meldrum, B. and Garthwaite, J. (1990) Excitatory amino acid neurotoxicity and neurodegenerative disease. *Trends Pharmacol. Sci.* 11:370–387.

Mochizuki, H., Nakamura, N., Nishi, K., and Mizuno, Y. (1994) Apoptosis is induced by 1-methyl-4-phenylpyridinium ion (MPP+) in ventral mesencephalic-striatal co-culture in rat. *Neurosci. Lett.* 170:191–194.

Monyer, H., Hartley, D. M., Choi, D. W. (1990) 21-aminosteroids attenuate excitotoxic neuronal injury in cortical cell cultures. *Neuron* 5:121–126.

Olanow, C. W. (1990) Oxidation reactions in Parkinson's disease. *Neurol.* 40:32–37.

Ratan, R. R., Murphy, T. H., and Baraban, J. M. (1994) Oxidative stress induces apoptosis. *J. Neurochem.* 62:376–379.

Raff., M. (1992) Social control on cell survival and cell death. *Nature* 356:397–400.

Rose, K., Goldberg, M. O. and Choi, D. W. (1992) Cytotoxicity in murine neocortical cell culture. In *In Vitro Biological Systems, Methods in Toxicology,* C. A. Tyson and J. M. Frazier, eds. (New York: Academic Press) vol. 1, pp. 46–60.

Rosen, D. R., Siddique, T., Patterson, D., Figlewicz, D. A., Sapp, P., Hentati, A., Donaldson, D., Goto, J., O'Regan, J. P., Deng, H. X. et al..(1993) Mutations in Cu/Zn superoxide dismutase gene are associated with familial amyotrophic lateral sclerosis. *Nature* 362:59–62.

Rosenthal, R. E., Chanderbhan, R., Marshall, G., Fiskum, G. (1992) Prevention of post-ischemic brain lipid conjugated diene production and neurological injury by hydroxyethyl starch-conjugated deferoxamine. *Free Rad. Biol. Med.* 12:29–33.

Rothman, S. M., and Olney, J. W. (1986) Glutamate and the pathophysiology of hypoxic-ischemic brain damage. *Ann. Neurol.* 19:105–111.

Rothstein, J., Bristol, L. A., Hosler, B., Brown, R. H., Jr, Kuncl, R. W. (1994) Chronic inhibition of superoxide dismutase produces apoptotic death of spinal neurons. *Proc Natl Acad Sci USA* 91:4155–4159.

Sheardown, M. J., Nielsen, E. O., Hansen, A. J., Jacobsen, P., Honore, T. (1990) 2,3-dihydroxy-6-nitro-7-sulfamoyl-benzo(F)quinoxaline: A neuroprotectant for cerebral ischemia. *Science* 247:571–574.

Siesjo, B. K., Agardh, C. D., and Bengtsson, F. (1989) Free radicals and brain damage. *Cerebrovasc. Brain Metab. Rev.* 1: 165–211.

Siesjo, B. K., Rehncrona, S., Smith, D. (1980) Neuronal cell damage in the brain: possible involvement of oxidative mechanisms. *Acta Physiol. Scand. [Suppl]* 492: 121–128.

Simon, R. P., Swan, J. H., Griffiths, T., Meldrum, B. S. (1984) Blockade of N-methyl-D-aspartate receptors may protect against ischemic damage in the brain. *Science* 226:850–852.

Stewart, B. W. (1994) Mechanisms of apoptosis: integration of genetic, biochemical and cellular indicators. *J. Natl. Cancer Inst.* 86:1286–1295.

Troy, C. M. and Shelanski, M. L. (1994) Down-regulation of copper/zinc superoxide dismutase causes apoptotic death in PC12 neuronal cells. *Proc Natl Acad Sci USA* 91:6384–6387.

Verity, M. A. (1994) Oxidative damage and repair in the developing nervous system. *Neurotoxicol.* 15:81–91.

Wideau-Pazos, M., Goto, J. J., Rabizadeh, S., Gralla, E. B., Roe, J. A., Lee, M. K., Valentine, J. S., Bredesen, D. E. (1996) Altered reactivity of superoxide dismutase in familial amyotrophic lateral sclerosis. *Science* 271:515–518.

Yoshiyama, Y., Yamada, T., Asanuma, K., Asahi, T. (1994) Apoptosis related antigen, Le(Y) and nick-end labeling are positive in spinal motor neurons in amyotrophic lateral sclerosis. *Acta Neuropathol (Berl)* 88:207–211.

Yue, T. L., Gu, J. L., Lysko, P. G., Cheng, H. Y., Barone, F. C., Feuerstein, G. (1992) Neuroprotective effects of phenyl-t-butyl-nitrone in gerbil global brain ischemia and in cultured rat cerebellar neurons. *Brain Res.* 574:193–197.

What is claimed is:

1. A method of treating neurotoxic injury in a patient suffering said injury by administering to said patient a composition comprising a compound of the formula $C_{60}(C(COOH)_2)_n$ wherein n is an integer from 1 to 4, its pharmaceutically acceptable salts and pharmaceutically acceptable esters, and a pharmaceutically acceptable carrier, wherein said compound is present in said composition in an amount effective to treat said neurotoxic injury.

2. The method of claim 1 wherein n is 3.

3. The method of claim 2 wherein said compound is O-3a.

4. The method of claim 3 wherein said compound is administered in an amount from about 1.5 mg/kg to about 1500 mg/kg daily.

5. The method of claim 4 wherein said compound is administered in an amount from about 10 mg/kg to about 60 mg/kg daily.

6. The method of claim 5 wherein said composition is administered orally.

7. The method of claim 5 wherein said composition is administered intravenously.

8. A method of inhibiting neurotoxic injury in a patient where said injury is caused by free radical oxygen species released by neurons due to the stimulation by glutamate of NMDA receptors of said neurons by administering to said patient a composition comprising a compound of the formula $C_{60}(C(COOH)_2)_n$ wherein n is an integer from 1 to 4, its pharmaceutically acceptable salts and pharmaceutically acceptable esters, and a pharmaceutically acceptable carrier, wherein said compound is present in said composition in an amount effective to inhibit said neurotoxic injury.

9. The method of claim 8 wherein n is 3.

10. The method of claim 9 wherein said compound is O-3a.

11. The method of claim 10 wherein said compound is administered in an amount from about 1.5 mg/kg to about 1500 mg/kg daily.

12. The method of claim 11 wherein said compound is administered in an amount from about 10 mg/kg to about 60 mg/kg daily.

13. The method of claim 12 wherein said composition is administered orally.

14. The method of claim 12 wherein said composition is administered intravenously.

15. A method of treating stroke in a patient by administering to said patient a composition comprising a compound of the formula $C_{60}(C(COOH)_2)_n$ wherein n is an integer from 1 to 4, its pharmaceutically acceptable salts and pharmaceutically acceptable esters, and a pharmaceutically acceptable carrier, wherein said compound is present in said composition in an amount effective to treat said stroke.

16. The method of claim 15 wherein n is 3.

17. The method of claim 16 wherein said compound is O-3a.

18. The method of claim 17 wherein said compound is administered in an amount from about 1.5 mg/kg to about 1500 mg/kg daily.

19. The method of claim 18 wherein said compound is administered in an amount from about 10 mg/kg to about 60 mg/kg daily.

20. The method of claim 19 wherein said composition is administered orally.

21. The method of claim 19 wherein said composition is administered intravenously.

22. A method of treating amyotrophic lateral sclerosis in a patient by administering to said patient a composition comprising a compound of the formula $C_{60}(C(COOH)_2)_n$ wherein n is an integer from 1 to 4, its pharmaceutically acceptable salts and pharmaceutically acceptable esters, and a pharmaceutically acceptable carrier, wherein said compound is present in said composition in an amount effective to treat said amyotrophic lateral sclerosis.

23. The method of claim 22 wherein n is 3.

24. The method of claim 23 wherein said compound is O-3a.

25. The method of claim 24 wherein said compound is administered in an amount from about 1.5 mg/kg to about 1500 mg/kg daily.

26. The method of claim 25 wherein said compound is administered in an amount from about 10 mg/kg to about 60 mg/kg daily.

27. The method of claim 26 wherein said composition is administered orally.

28. The method of claim 26 wherein said composition is administered intravenously.

* * * * *